(12) United States Patent
Ellis

(10) Patent No.: US 8,337,402 B1
(45) Date of Patent: Dec. 25, 2012

(54) AMBIDEXTROUS LARYNGOSCOPE BLADE

(76) Inventor: Charles W. Ellis, Beaumont, TX (US)

( * ) Notice: Subject to any disclaimer, the term of this patent is extended or adjusted under 35 U.S.C. 154(b) by 1316 days.

(21) Appl. No.: 11/437,944

(22) Filed: May 19, 2006

(51) Int. Cl.
*A61B 1/267* (2006.01)

(52) U.S. Cl. .................................... 600/199; 600/189

(58) Field of Classification Search .......... 600/240–241, 600/184–200; D24/135–139; 606/194
See application file for complete search history.

(56) References Cited

U.S. PATENT DOCUMENTS

| | | | | |
|---|---|---|---|---|
| 79,015 | A * | 6/1868 | Schulz | 128/200.15 |
| 374,122 | A * | 11/1887 | Genese | 600/240 |
| 2,240,402 | A * | 4/1941 | Joroslow | 385/33 |
| 2,433,705 | A | 12/1947 | Palmeter | |
| 3,638,644 | A * | 2/1972 | Reick | 600/191 |
| 4,114,609 | A * | 9/1978 | Moses | 600/193 |
| 4,360,008 | A | 11/1982 | Corazzelli, Jr. | |
| 4,394,235 | A | 7/1983 | Brandt et al. | |
| 4,573,451 | A | 3/1986 | Bauman | |
| 4,596,239 | A | 6/1986 | Bauman | |
| 4,607,623 | A | 8/1986 | Bauman | |
| 4,799,485 | A | 1/1989 | Furey et al. | |
| 4,827,910 | A | 5/1989 | Mathews, III | |
| 4,832,004 | A | 5/1989 | Heckele | |
| 4,947,896 | A * | 8/1990 | Bartlett | 600/187 |
| 4,996,976 | A * | 3/1991 | Nakagawa | 600/212 |
| 5,178,132 | A | 1/1993 | Mahefky | |
| 5,363,840 | A | 11/1994 | Silva | |
| 5,438,976 | A | 8/1995 | Nash | |
| 5,542,905 | A | 8/1996 | Nussenbaum | |
| 5,551,946 | A | 9/1996 | Bullard | |
| 5,584,795 | A | 12/1996 | Valenti | |
| 5,651,760 | A | 7/1997 | Upsher | |
| 5,665,052 | A | 9/1997 | Bullard | |
| 5,695,454 | A | 12/1997 | Mourkidou | |
| 5,772,581 | A | 6/1998 | Gaines | |
| 5,938,591 | A | 8/1999 | Minson | |
| 6,045,499 | A * | 4/2000 | Pitesky | 600/240 |
| 6,095,972 | A | 8/2000 | Sakamoto | |
| 6,217,514 | B1 | 4/2001 | Gruen et al. | |
| 6,231,505 | B1 * | 5/2001 | Martin | 600/194 |
| 6,454,704 | B1 | 9/2002 | Dzwonkiewicz | |
| 6,764,443 | B1 | 7/2004 | Watson | |
| 7,909,757 | B2 * | 3/2011 | Herman | 600/190 |
| 2004/0210115 | A1 * | 10/2004 | Ma et al. | 600/199 |
| 2007/0232862 | A1 * | 10/2007 | Herman | 600/190 |

FOREIGN PATENT DOCUMENTS

| EP | 339541 | A1 * | 11/1989 |
|---|---|---|---|
| EP | 494840 | A1 * | 7/1992 |

OTHER PUBLICATIONS

Machine translation of EP 339541 Al.*

* cited by examiner

*Primary Examiner* — Kevin T Truong
*Assistant Examiner* — Larry E Waggle, Jr.
(74) *Attorney, Agent, or Firm* — Charles W. Hanor

(57) ABSTRACT

An improved laryngoscope blade for use with a conventional laryngoscope handle and conventional means of illumination. The blade tapers from the handle end to the end that is inserted in the mouth, so that the blade roughly conforms to the shape of the tongue. In addition, the sides of the blade curve upward so as to cradle the tongue. This design allows the intubator to better control the tongue and more easily view the vocal chords during insertion of an endotracheal tube. Furthermore, the ambidextrous, symmetrical design is easier for left-handed doctors and technician to use.

7 Claims, 6 Drawing Sheets

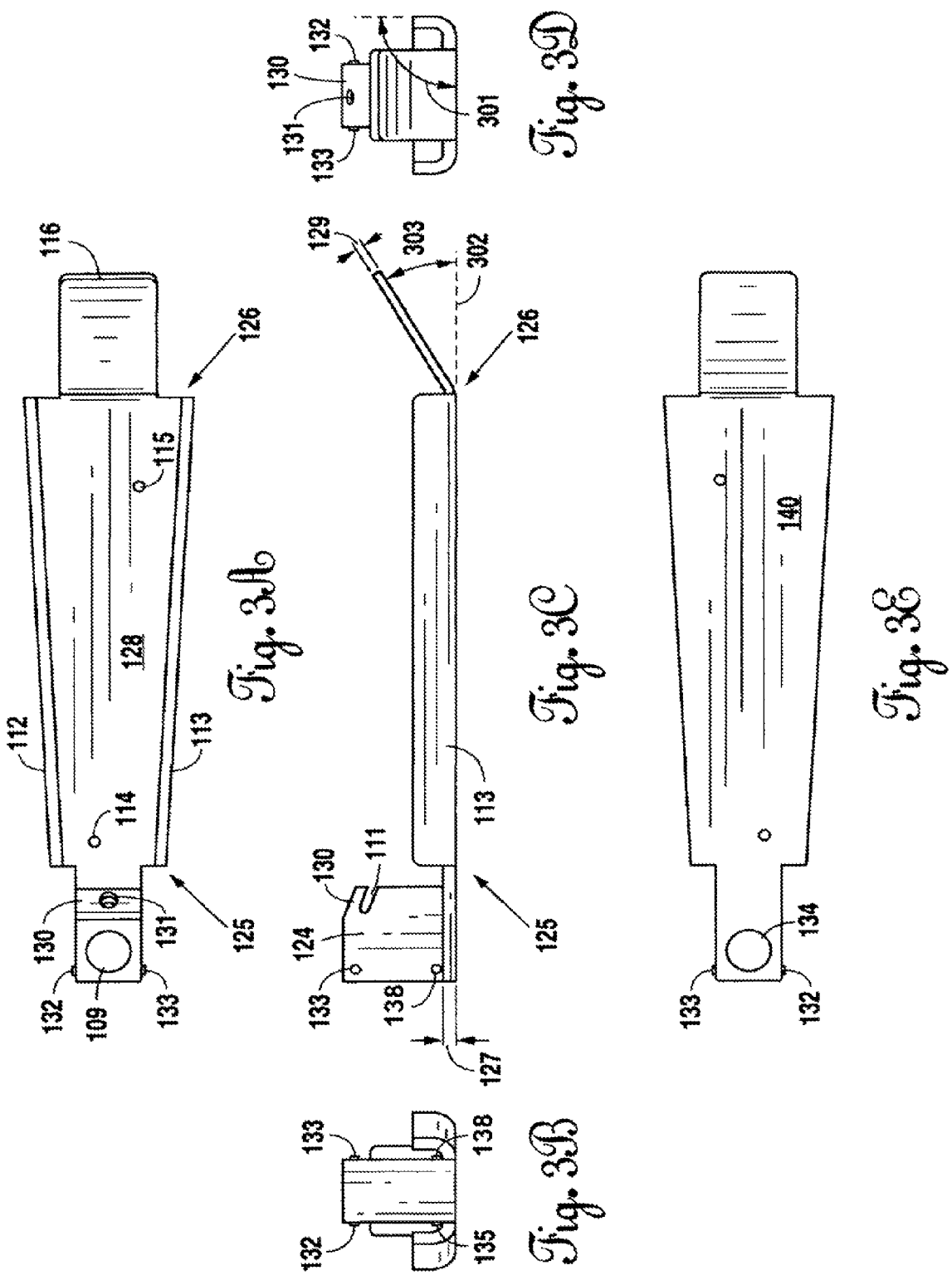

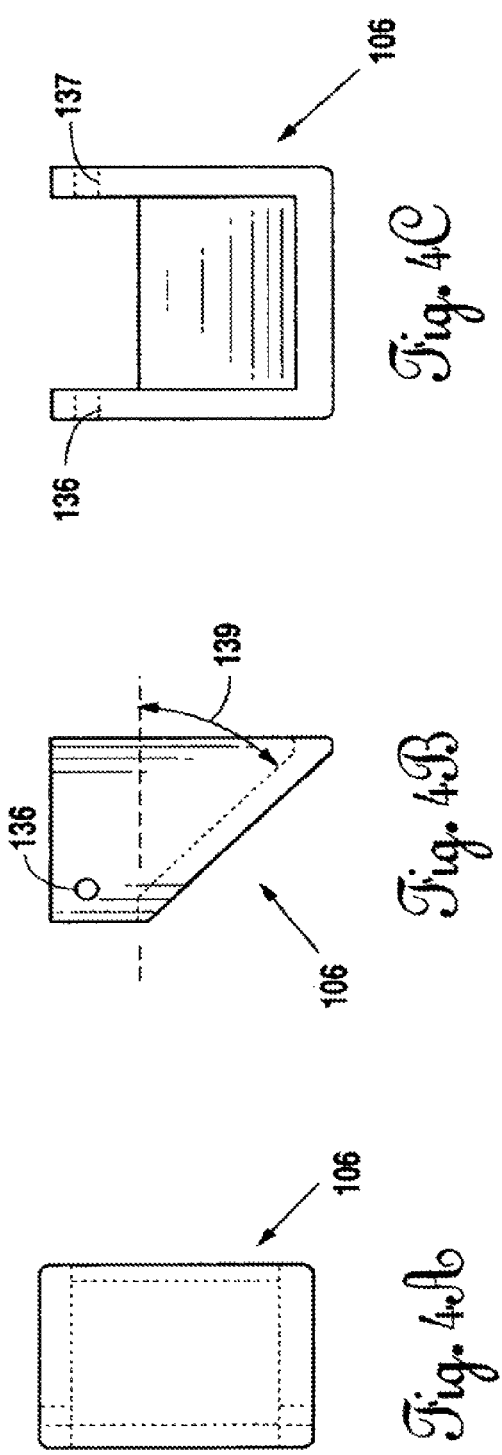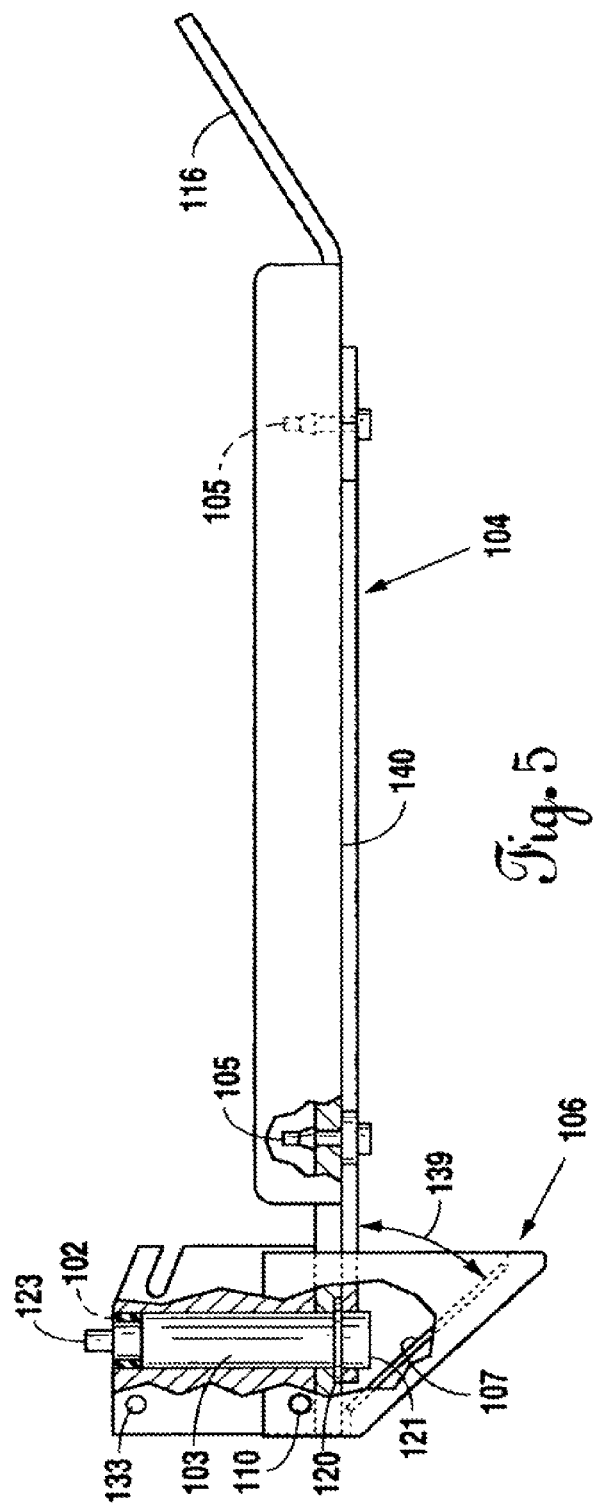

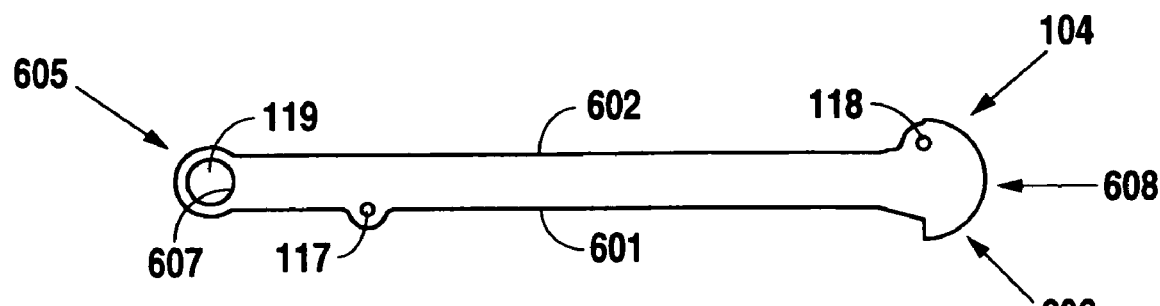
Fig. 6A
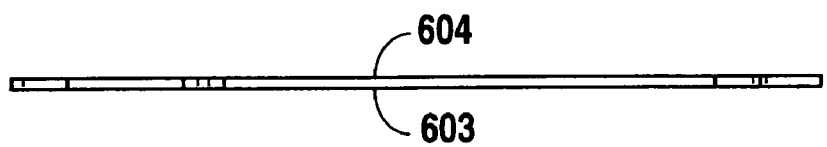
Fig. 6B
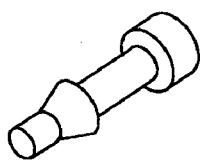
Fig. 6C
 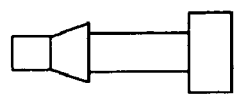
Fig. 6D    Fig. 6E

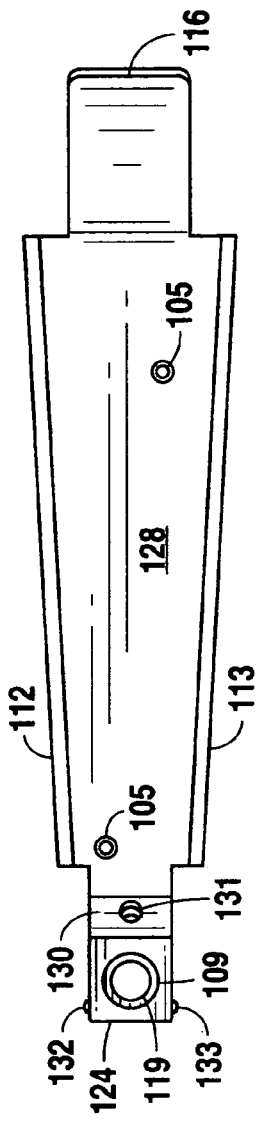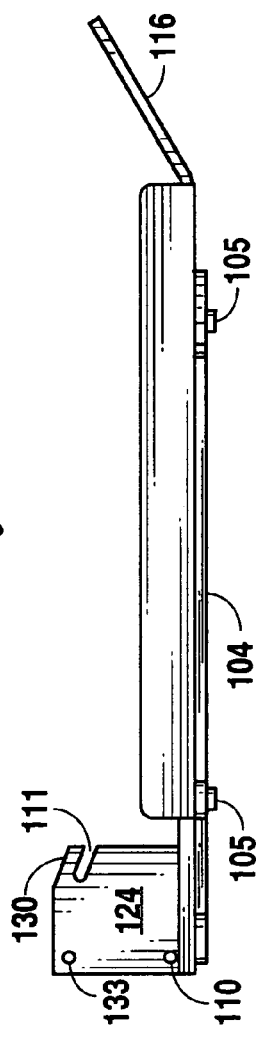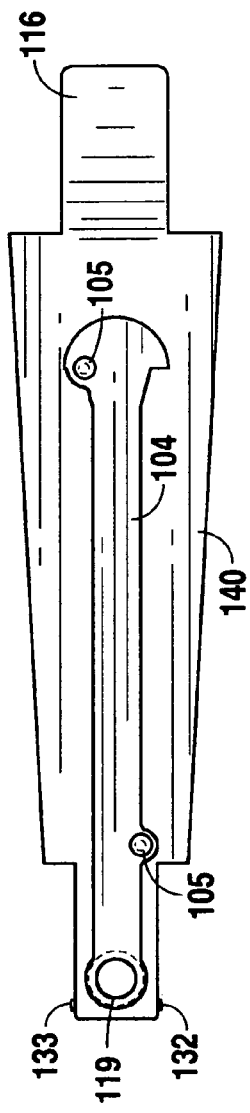

AMBIDEXTROUS LARYNGOSCOPE BLADE

CROSS-REFERENCE TO RELATED APPLICATIONS

N/A

STATEMENTS REGARDING FEDERALLY SPONSORED RESEARCH OR DEVELOPMENT

N/A

REFERENCE TO A MICROFICHE APPENDIX

N/A

BACKGROUND OF THE INVENTION

1. Field of the Invention

The present invention relates to a laryngoscope, which is a device used in an endotracheal intubation procedure. In particular, this invention is an improved design for the blade of a laryngoscope.

2. Description of the Related Art

While a laryngoscope may be used for inspection of the upper airway for possible foreign body obstruction or to visualize the larynx, the primary purpose of the laryngoscope is to visualize the vocal chords prior to insertion of an endotracheal tube during intubation. The need for such intubation may arise during a controlled situation, such as pre-surgery, or in a crisis situation where the patient is unable to breathe adequately and requires advanced airway interventions.

In order to intubate the patient, the intubator (either a physician or trained technician) must have a clear view of the vocal chords to insure the tube enters between the chords and not down the esophagus. When the body is in the supine position and the head is in the normal anatomic position the airway is narrowed and the tongue itself may possibly become an obstructing factor. It is therefore recommended that the intubator be able to secure the tongue and visualize the vocal chords as rapidly as possible. The laryngoscope itself generally comprises a handle and a blade. The intubator will hold the handle in one hand and position the blade against the patient's tongue. The intubator will use the edge of the blade to push the tongue to one side and the tip of the blade to lift the epiglottis, exposing the vocal chords. The handle will generally contain a light source which will illuminate the vocal chords. The intubator will then use her free hand to insert the tube between the patient's vocal chords.

In the current state of the art, the two most widely used blades as Miller blades and Macintosh blades. A Miller blade is a substantially straight blade with a curved tip, the curve commencing approximately 2 inches from the end of the blade. A Macintosh is a blade which is curved substantially its entire length (U.S. Pat. No. 2,354,471. Issued Jul. 25, 1944). In practice, the Miller blade is inserted along the longitudinal axis of the larynx past the epiglottis to lift it enough to visualize the vocal chords and slip the endotracheal tube between the chords and into the trachea. The Macintosh blade is inserted on a combination of the axis of the oral cavity and the longitudinal axis of the larynx, the tip being placed in the vallecula, which is the shallow depression in the membranous folds of tissue between the epiglottis and the roof of the tongue. By applying upward pressure at the vallecula, the epiglottis is raised enough to visualize the vocal chords.

While both Miller blades and Macintosh blades are adequate for performing intubation, both types of blade designs leaves three problems unsolved. First, prior art blades are designed such that in order to visualize the vocal chords, the doctor or technician will operate the laryngoscope with one hand and intubate the patient with the other hand. Standard blades are designed for right handed people; that is, the blade is operated with the left hand and the intubation is done with the dominant right hand. Left handed people either require different blades or are required to wield the tool in their dominant hand and attempt intubation, which is a delicate procedure, with their non-dominant hand. A second problem with prior art blades is that they do not include adequate means for securing the tongue. The tongue is always wet and tends to slide off the edge of a standard laryngoscope blade. Lastly, and partially as a result of the first two design shortcomings, current state of the art blades do not provide a sufficient view of the field of work (i.e. the vocal chords), because these tools do not provide an adequate angle of address for the vocal chords and allow unsecured portions of the tongue to block the field of view.

While there have been efforts to improve blade design, none of the improvements, taken either singularly or in combination, adequately address the aforementioned problems. Efforts to improve the curvature of the blade are shown in U.S. Pat. No. 5,003,962, issued Apr. 2, 1991 to Choi, and U.S. Pat. No. 5,406,941 issued Apr. 18, 1995 to Roberts. Choi describes a blade having 3 straight segments, the second segment at a 20 degree angle to the first, and the third at a 30 degree angle to the second. The Roberts patent describes a flat, flexible blade, having a cam attached to one side of the blade so the curvature may be adjusted by rotating the cam. U.S. Pat. No. 3,856,001 issued to O.C. Phillips Dec., 24, 1974 describes a Jackson or straight blade having a "U" shaped cross section and a tip similar to the Miller blade, curving about 2 inches from its end.

Efforts to improve the tip are shown in U.S. Pat. No 4,573,451, issued Mar. 4, 1986 to Bauman, and U.S. Pat. No. 5,603,688 issued Feb. 18, 1997 to Upsher. The Bauman patent describes a blade made of plastic or metal, thinning or hinged at the tip, with a push rod and ratchet to change the angle of the tip. Upsher's patent shows a blade having a hollow tube in the side of the tip to prevent the natural curve of the endotracheal tube to leave the field of vision after exiting the hollow tube in the blade.

Efforts to improve the illumination of the larynx and vocal chords are shown in U.S. Pat. No. 3,771,514 issued Nov. 13, 1973 to Huffman, and in U.S. Pat. No. 3,638,644 issued Feb. 1, 1972 to Reick. The Reick patent shows a light bulb in the handle with a plastic light conduit extending through the blade. The Huffman patent shows a one piece handle and blade, the blade having a prism mounted thereon for reflecting and diffusing light.

These inventions leave the three aforementioned problems unsolved.

BRIEF SUMMARY OF THE INVENTION

Accordingly, it is a principal object of this invention to provide an improved laryngoscope blade which allows better visualization of the vocal chords, ambidextrous usability, and vast improvement in control of the tongue during the procedure.

The present invention is a laryngoscope blade which is generally straight throughout its length but appears inverted when compared to current state of the art laryngoscope blades. In addition, the blade has upturned edges to better control the tongue, a reengineered tip to better access the vallecula, and a unique proximal angle to insure there is no contact between the laryngoscope blade and the teeth.

The laryngoscope blade of the present invention is tapered to better approximate the true anatomy of the tongue. This allows the intubator superior control of the tongue during an intubation procedure or during an examination of the airway. This configuration is unlike the design of conventional laryngoscope blades.

BRIEF DESCRIPTION OF THE SEVERAL VIEWS OF THE DRAWINGS

FIG. 3A. Top view of laryngoscope blade without mirror base, light bar, or light bulb attached.

FIG. 3B. View of the proximal end of the laryngoscope blade without mirror base, light bar, or light bulb attached.

FIG. 3C. Side view of laryngoscope blade without mirror base, light bar, or light bulb attached.

FIG. 3D. View of the distal end of the laryngoscope blade without mirror base, light bar, or light bulb attached.

FIG. 3E. Bottom view of laryngoscope blade without mirror base, light bar, or light bulb attached.

FIG. 4A. View of the proximal end of the mirror base.

FIG. 4B. Side view of mirror base.

FIG. 4C. View of the distal end of the mirror base.

FIG. 5. Side view of assembled laryngoscope with mirror base attached and cutaway views at locking mechanism for light bar and at mirror base.

FIG. 6A. Top view of light bar.

FIG. 6B. Side view of light bar.

FIG. 6C. Three-dimensional view of rubber plug used to secure light bar to laryngoscope.

FIG. 6D. Bottom view of rubber plug used to secure light bar to laryngoscope.

FIG. 6E. Side view of rubber plug used to secure light bar to laryngoscope.

FIG. 7A. Top view of laryngoscope with light bar attached.

FIG. 7B. Side view of laryngoscope with light bar attached.

FIG. 7C. Bottom view of laryngoscope with light bar attached.

DETAILED DESCRIPTION OF THE INVENTION

Figure 1:
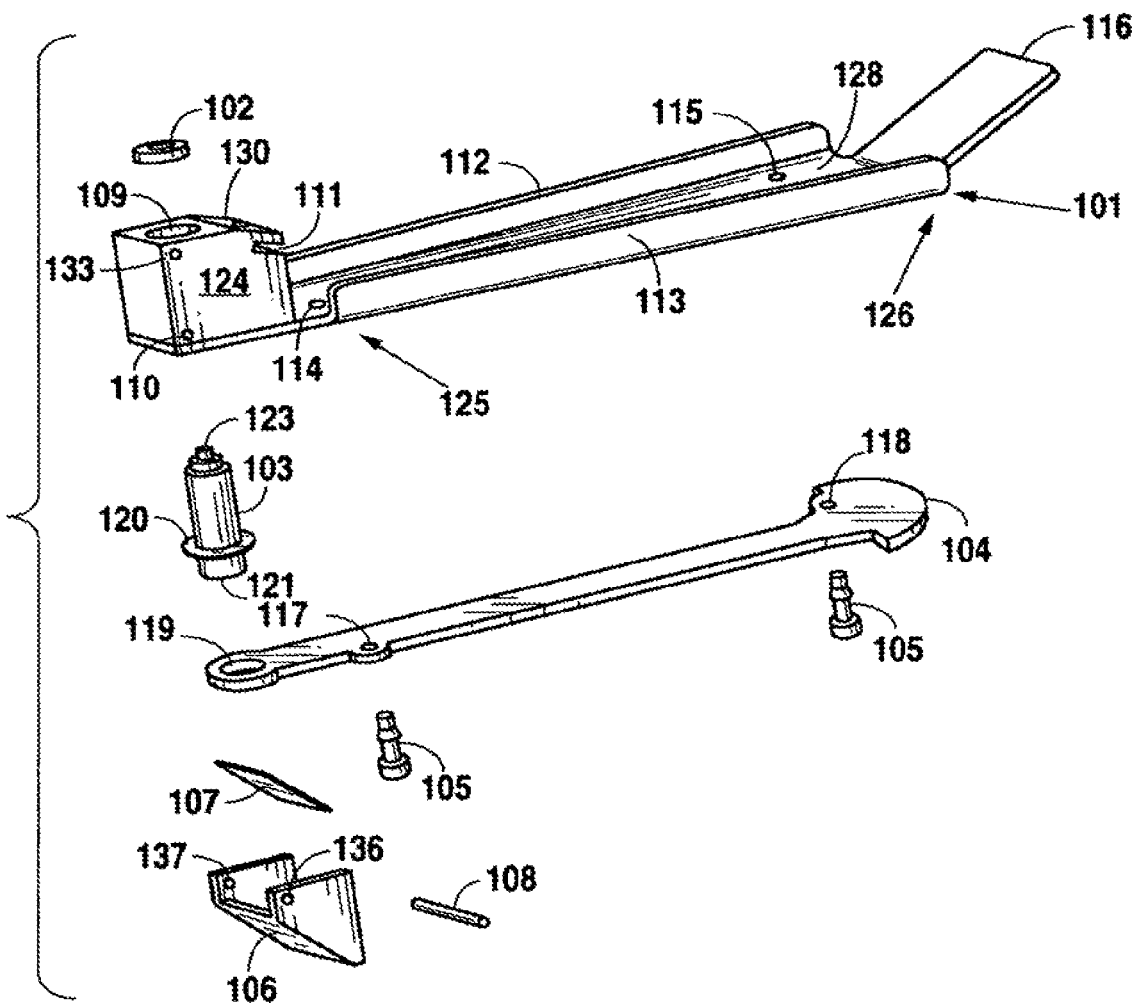
FIG. 1. Three-dimensional view of laryngoscope broken into its component parts.

FIG. 1 shows the disassembled components of the laryngoscope. The major components include the blade 101, the mirror base 106, the light bar 104, and the light source 103. The other major components of a laryngoscope not shown in FIG. 1 is a handle 801. The present invention comprises the unique designs of the blade 101, mirror base 106, and light bar 104, which can operate with a wide variety of light sources 103 and handles 801 that are well known in the field of art.

Figure 8:
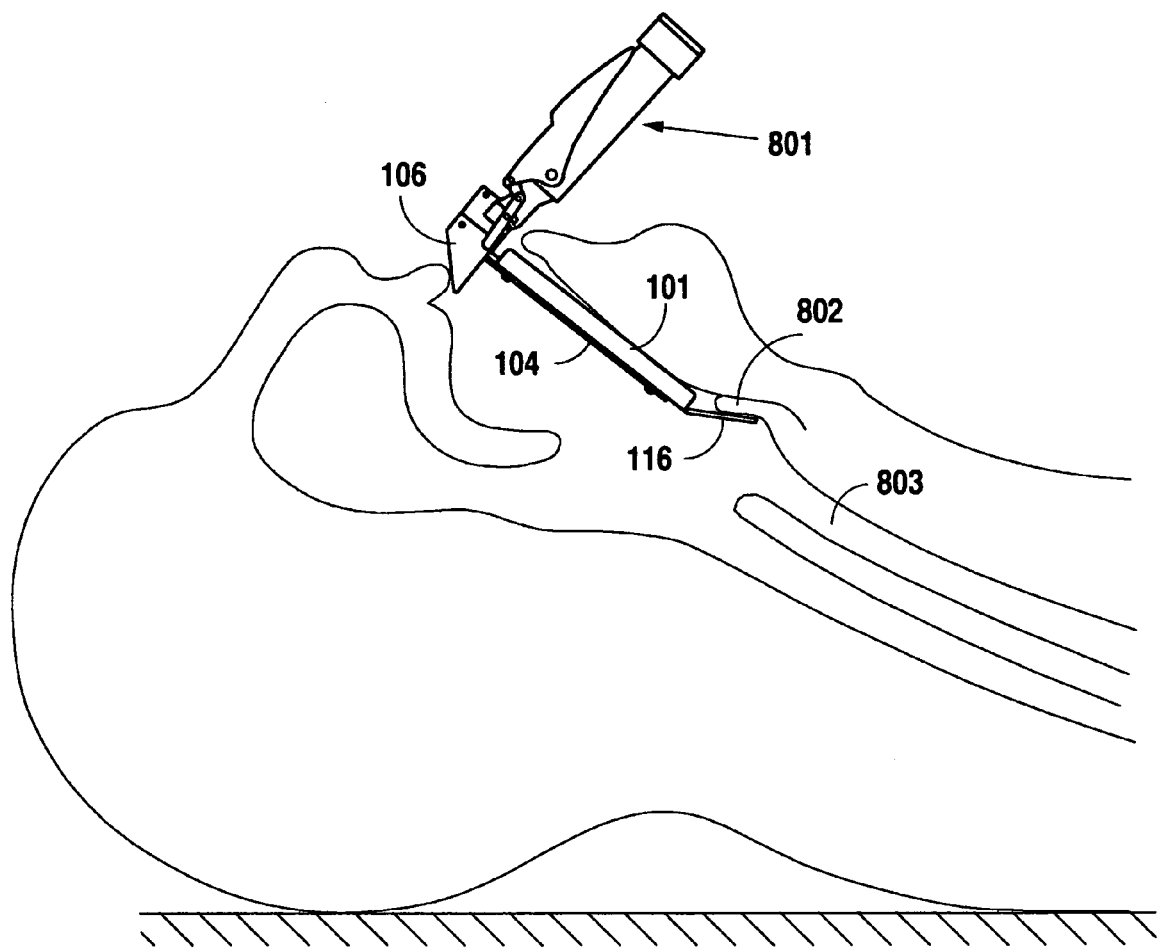
FIG. 8. Patient's head with laryngoscope blade in use.

The blade 101 is the central component of the laryngoscope. It is used to hold the tongue out of the visual path of the intubator. As depicted in FIG. 8, it is also used to apply pressure to the epiglottic vallecula 802 and thereby physically expose the vocal chord and trachea 803. The blade 101 also comprises a block housing 124. The block housing may house a light source 103, can attach to a handle 801, and can attach to a mirror base 106. In addition, a light bar 104 may be attached to the base 128 of the blade 101 to improve illumination in the mouth and throat of the patient. The blade 101 and mirror base 106 are preferably made of stainless steel. The light bar 104 is preferably made of plexiglass.

To intubate a patient, an intubator will insert the blade 101 into the mouth of the patient. The blade may be positioned to hold the tongue out of the visual path of the intubator. The width of the blade is tapered from the distal end 126 to the proximal end 125. The taper closely matches the anatomy of a tongue to give the intubator better control over tongue position. The angle of taper is also calculated to ensure that there is no contact between the device and the patient's teeth. In an ideal embodiment, the width of the blade at the proximal end is between 30% and 40% of the width of the blade at the distal end. Generally, the width of the proximal end will measure between 2 and 4 centimeters and the width of the distal end will measure between 6 and 10 centimeters. The thickness 127 of the base 128 of the blade 101 is uniform and the blade's upper and lower flat surfaces are smooth. The edges 112 and 113 of the base 128 of the blade 101 are raised at an angle 301 sufficient to stabilize the position of the tongue when the laryngoscope blade is in use.

Once the tongue is stabilized and out of the visual path of the intubator, she will use the tab 116 at the distal end 126 of the blade 101 to apply pressure to the epiglottal vallecula, thus raising the epiglottis and exposing the vocal chords and trachea. The tab 116 extends upward from the base's plane 302 in the same direction as the raised edges 112 and 113 at a fixed angle 303 which approximately conforms to the anatomy of a patient's mouth. To apply pressure on the vallecula, the intubator must raise the proximal end 125 of the blade, thereby lowering the tab 116 onto the vallecula. If angle 303 is too shallow, there will be insufficient room in the patient's mouth to apply ample pressure to the vallecula. If the angle 303 is too great, there may be insufficient room to fit the blade 101 and tab 116 into the rear portion of the patient's mouth. In the preferred embodiment the angle 303 is approximately 30 degrees. After additional experimentation, it may be desirable to change this angle slightly to improve the laryngoscope or to create a laryngoscope for special patients, (e.g. children). The thickness 129 of the tab may be different than the thickness 127 of the blade base 128 from which it extends.

The laryngoscope blade may also comprise a block housing 124 at the proximal end 125 of the blade. The block housing 124 is designed to provide several functions. First, the block housing will allow for the attachment of a handle 801. To provide the greatest compatibility with the existing prior art laryngoscope handles, the block housing will comprise a variety of means for attaching a handle including an angled slot 111, an angled face 130 with a hole 131, and ball latch pins 132 and 133. The handle may comprise a power source, such as dry cell batteries, to provide power to a light source.

The block housing 124 is designed to also house an industry-standard light source 103. The light source 103 will be inserted through a hole 109 in the upper side of the block housing 124. The contact end 123 of the light source 103 will connect to the handle 801. The light source will be held in place by a grommet 102 at its upper end and a ridge 120 near its lower end. The illuminating end 121 fits in a hole 134 at the proximal end 125 of the base 128 of the blade 101.

Figure 2:
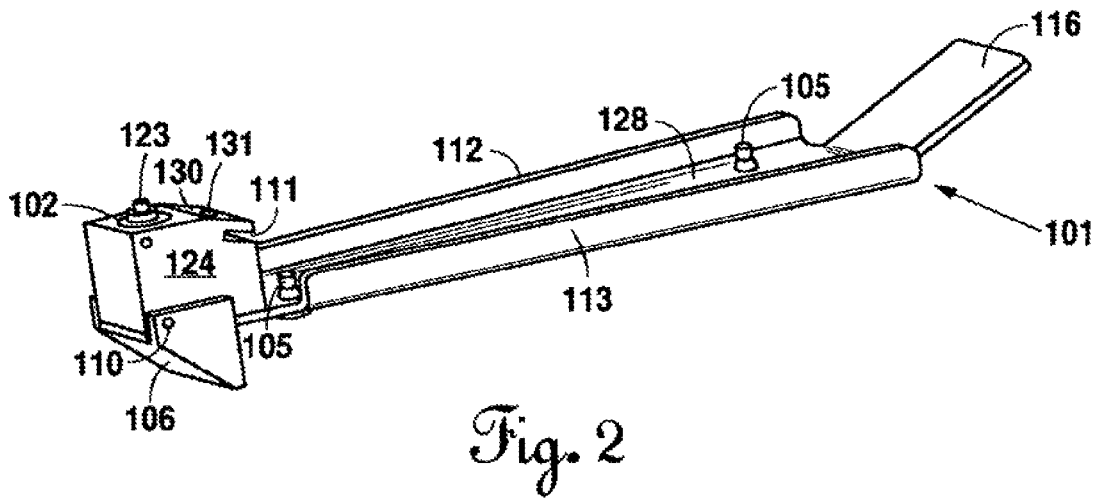
FIG. 2. Three-dimensional view of laryngoscope assembled.

There are two alternative embodiments to improve illumination in the back of the patient's mouth. In one embodiment, a mirror base 106 is attached at the proximal end 125 of the base 128 of the blade 101, as depicted in FIG. 2 and FIG. 5. The mirror base may comprise holes 136 and 137 that will be used to attach the mirror base 106 to the block housing 124 in one of two alternative methods. First, the block housing may have a hole 110 at its lower end and connecting rod 108 will be inserted through hole 136, 110, and 137 to hold the mirror base in place. Secondly, the block housing may have ball latch pins 138 and 135 at its lower end which will compress when the mirror base is pushed over the block housing and release when the holes 136 and 137 of the mirror base are aligned over the ball latch pins 138 and 135. The mirror base 106 will have a sloped base at a 45-degree angle 139. When a mirror 107 is affixed to this sloped base, the light source will be reflected from the proximal end 125 to the distal end 126 of the blade 101 (i.e. toward the rear of the patient's mouth).

An alternative embodiment to improve illumination uses a light bar 104 to reflect light from the light source into the mouth. The light bar 104, as depicted in FIG. 6, is made of an opaque material (such as acrylic or plexiglass). It rests along the lower surface 140 of the blade 101 and is secured in place by pushing two rubber plugs 105 through two holes 117 and 118 on the light bar and two holes 114 and 115 on the base 128 of the blade. The sides 601 and 602, bottom surface 603, and top surface 604 of the light bar 104 are black faced so as to prevent light from passing through. There is a hole 119 on the proximal end 605 of the light bar 104 into which the illuminating end 121 of the light source will fit. The inner circumference 607 of the hole 119 is clear such that light may enter the light bar 104 through this inner surface 607. At its distal end 606 the light bar 104 terminates in a half circle shape. The outer circumference 608 of this half circle is also clear such that light may be emitted through the outer circumference 608.

FIG. 8 shows the laryngoscope in use with both mirror base 106 and light bar 104 attached. The drawing shows both the mirror base 106 and the light bar 104 only for demonstrative purposes. In practical use, either the light bar 104 or the mirror base 106, not both, would be used. The tongue is held in place by the blade 101. The tab 116 is used to depress the epiglottis 802. The intubator is then able to see through the upper trachea 803 to properly intubate the patient.

Unlike prior art laryngoscopes, this invention does not require that the tongue be pushed aside and held while the epiglottis is raised. Instead, because of the way the blade is designed, the tongue is held in place in its natural position by the base of the blade, while the angled tab moves the epiglottis. The blade design provides an optimal view of the trachea and exposed vocal cords. The device can easily be used in either hand since the blade is symmetrically tapered and since the paired raised edges hold the tongue in place, rather than move it to one side or the other. Endotracheal intubation is sometimes done in preparation for surgery, but is often done under emergency circumstances, when time is of the essence. The present invention contains improvements which allow critical increases in the rapidity with which patients may be intubated.

What is claimed is:

1. A laryngoscope blade comprising:
   a base comprising a proximal end,
   a distal end dimensioned for insertion into a patient's mouth,
   a flat upper surface,
   a flat lower surface,
   a lateral axis extending from the proximal end to the distal end,
   a horizontal plane parallel to the upper surface, and
   two straight sides which angle upward in relation to the horizontal plane;
   wherein the base increases in width symmetrically along the lateral axis from the proximal end to the distal end;
   a tab extending from the distal end in the direction of the lateral axis and angling upward in relation to the horizontal plane, wherein the width of the tab at its connection to the distal end is less than the width of the distal end;
   a means to attach a handle to the blade; and
   a means for illuminating a patient's vocal chords comprising an opaque light bar attached to the lower surface of the base and running along the lateral axis of the base, wherein the light bar comprises a clear opening at the proximal end for a light source to fit such that light may enter the light bar, a termination of the light bar at the distal end such that light may be emitted, and black-faced sides, top, and bottom.

2. The laryngoscope blade of claim 1 where the width of the blade at the proximal end is no less than 2 cm and no more than 4 cm.

3. The laryngoscope blade of claim 1 wherein the width of the blade at the distal end is no less than 6 cm and no more than 10 cm.

4. The laryngoscope blade of claim 1 wherein the tab angles upward from the horizontal plane at an angle of between 15 and 45 degrees.

5. The laryngoscope blade of claim 1 including means for attaching a handle which comprises a block housing located on the upper surface of the base at the proximal end, wherein such block housing comprises a means for holding a light source.

6. The laryngoscope blade of claim 1 wherein the means for illuminating the vocal chords further comprises an angled mirror base attached on the lower surface of the base at the proximal end.

7. The laryngoscope blade of claim 1 wherein the light bar further comprises a half circle shape at the distal end termination.

* * * * *